United States Patent [19]
Friese

[11] 4,453,296
[45] Jun. 12, 1984

[54] APPARATUS FOR PRESSING WORKPIECES OF ABSORBENT MATERIAL, PARTICULARLY TAMPONS FOR FEMININE HYGIENE

[75] Inventor: Axel Friese, Wuppertal, Fed. Rep. of Germany

[73] Assignee: Dr. Carl Hahn, G.m.b.H., Dusseldorf, Fed. Rep. of Germany

[21] Appl. No.: 414,257

[22] PCT Filed: Dec. 21, 1981

[86] PCT No.: PCT/DE81/00231
§ 371 Date: Aug. 13, 1982
§ 102(e) Date: Aug. 13, 1982

[87] PCT Pub. No.: WO82/02335
PCT Pub. Date: Jul. 22, 1982

[30] Foreign Application Priority Data
Dec. 31, 1980 [DE] Fed. Rep. of Germany ....... 3049580

[51] Int. Cl.³ .............................................. A61F 13/20
[52] U.S. Cl. ..................................... 28/119; 425/236; 425/397; 425/408
[58] Field of Search ............... 425/383, 236, 397, 408, 425/804; 28/118, 119, 120

[56] References Cited
U.S. PATENT DOCUMENTS
2,263,302 11/1941 Johnson .............................. 425/444
3,131,435 5/1964 Cloots et al. .......................... 28/120
4,081,884 4/1978 Johst et al. ............................ 28/119

Primary Examiner—Donald E. Czaja
Assistant Examiner—Mary A. Becker
Attorney, Agent, or Firm—Jason Lipow

[57] ABSTRACT

Between a pre-shaping device and a pressing device for tampons there is interposed a delivery device. The longer parallel legs of the L-shaped pressing jaws are set at a distance which corresponds to the diameter of the tampon. The shorter legs of the pressing jaws are oriented towards the longer leg of the other pressing jaw. The width of the pressing jaws corresponds at least to the length of the tampon and of the withdrawal cord. The delivery device is arranged for reciprocating movement transversely of the pressing jaws and has a transmitting channel which corresponds to the opened pressing device as well as a receiving channel which corresponds to the closed pressing device. Also interposed along with the delivery device, and in alignment with the transmitting channel, there is a transmitting device, and there is also a transmitting device in alignment with the receiving channel and the ejecting channel. Behind the pressing device there is a cylindrical ejecting device which is movable in the closed pressing device for ejecting the tampon from the pressing device through the ejecting channel.

6 Claims, 8 Drawing Figures

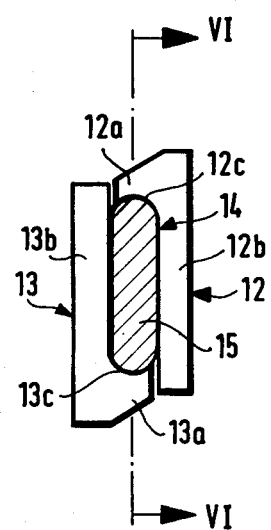
FIG. 3
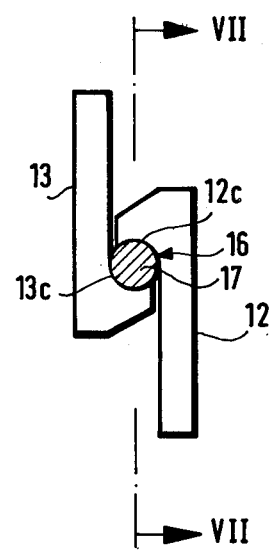
FIG. 4
FIG. 5
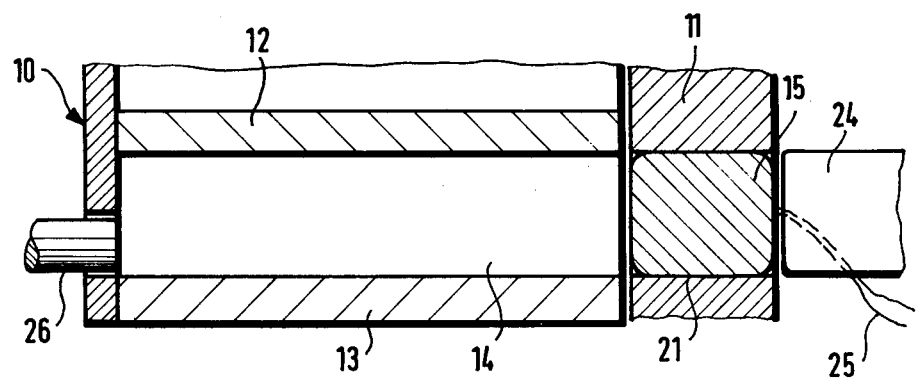

APPARATUS FOR PRESSING WORKPIECES OF ABSORBENT MATERIAL, PARTICULARLY TAMPONS FOR FEMININE HYGIENE

BACKGROUND OF THE INVENTION

This invention relates to improvements in an apparatus for pressing workpieces of absorbent material and particularly to improvements in the invention disclosed in U.S. Pat. No. 3,845,520 issued to Stefan Simon on Nov. 5, 1974 which patent is based on German application 2114530, filed in Germany on Mar. 25, 1971, and is referred to herein as "the main patent" and incorporated by reference.

The main patent relates to an apparatus for pressing workpieces of an absorbent material, particularly tampons for feminine hygiene, comprising an endless feeding device conveying the workpieces before open sides of a pre-shaping device and by means of at least one push-rod into said pre-shaping device; a transmitting device for transmitting the pre-shaped workpieces from the pre-shaping device to a pressing device and an ejecting device for ejecting the pressed workpieces from the pressing device, said pre-shaping device consisting of a number of pre-shaping jaws with opposite pre-shape counterholding jaws and said pressing device consisting of a number of pressing jaws with opposite counterholding jaws, the pressing jaws and the counterholding jaws comprising a substantially L-shaped working surface and the end of the short leg of each working surface lying against the long leg of the opposite working surface and the short legs of associated working surfaces being provided with oppositely disposed recesses such that in the closed position they form an approximately cylindrical cavity.

The main patent is based on the object to improve such an apparatus to the effect that it is particularly suitable for parallel operation and that the pressing process can be subdivided in such a way that the individual forces to be applied in a pre-shaping stage and a subsequent pressing stage can nevertheless be controlled with respect to magnitude and direction.

This problem is solved according to the main patent in that the pre-shaping jaws with associated pre-shape counterholding jaws and the pressing jaws with associated counterholding jaws are arranged about horizontally and that the number of jaws of the pressing device is equal to that of the pre-shaping device, the spaces formed by the jaws of the pressing device being disposed approximately in alignment with the spaces formed by the jaws of the pre-shaping device at the open sides of the pre-shaping device directed away from the feeding device, while the transmitting device consists of push-rods positioned on the same side as the feeding device.

SUMMARY OF THE INVENTION

The invention provides a further improvement of the apparatus according to the main patent in that workpieces consisting of absorbent material and having been provided already with a withdrawal cord can likewise be pressed, as according to the main patent, in an optimum manner, i.e., at a high production speed ensuring mass production and a high constancy of performance as well as to ensure a high quality of the product, wherein in particular the pressing of the workpiece without damaging of the withdrawal cord and after pressing a satisfactory pressing of the withdrawal cord against the end of the pressed workpiece, particularly tampons, is to be possible.

In reference to the specific apparatus described in the main patent it can be seen that due to the interposition of a delivery device between pre-shaping device and pressing device, it is possible to eject in the delivery position of the delivery device the blank from the pre-shaping device into the pressing device and simultaneously to eject a tampon positioned in the delivery device from the latter, while the delivery device in the receiving position takes over a just pressed tampon from the press, said taking-over movement being simultaneously utilized for pressing the withdrawal cord against the withdrawal end of the tampon when the tampon has reached the delivery device. Due to the fact that the pressing jaws and the counterholding jaws of the pressing device are wider than the total length of the blank/tampon plus the free length of the withdrawal cord attached thereto and that the short legs of the pressing jaws lie against the opposite working surfaces, an undisturbed handling of the withdrawal cord is ensured during the final pressing of the blank to a tampon. Since with the ejection movement of the completely pressed tampon from pressing device there is simultaneously combined the step of pressing the withdrawal cord to the withdrawal end of the tampon, there are saved an additional working step and the provision of additional pressing means for carrying out that work.

The design of the transmitting channel in the delivery device as well as of the transmitting device as described herein ensures that the blank is completely imparted by the transmitting device and thus an undisturbed transport of the blank into the pressing device.

The design of the receiving channel in the delivery device as described herein ensures that the push-rod of the transmitting device, which corresponds to the cross-section of the blank, closes the receiving channel and serves as abutment for the tampon ejected from the pressing device, when the withdrawal cord is pressed against the end of the tampon directed away from the push-rod of the transmitting device by means of the push-rod of the ejecting device.

The ejecting channel as described herein in the housing of the pressing device ensures a form-closed delivery of the tampon to a further processing station, e.g. packing station.

BRIEF DESCRIPTION OF THE DRAWINGS

In the following the invention is explained in more detail by means of a schematic drawing of an embodiment, in which

FIG. 3 shows the cavity between the open jaws of the pressing device, filled with a blank;

FIG. 4 shows the cylindrical cavity of the closed pressing jaws of the pressing device with a tampon completely pressed therein;

FIG. 5 shows a section along line V—V in FIG. 2 in the delivery position of the delivery device with a blank in the transmitting channel thereof with open pressing device;

DESCRIPTION OF THE PREFERRED EMBODIMENTS

Figure 1:
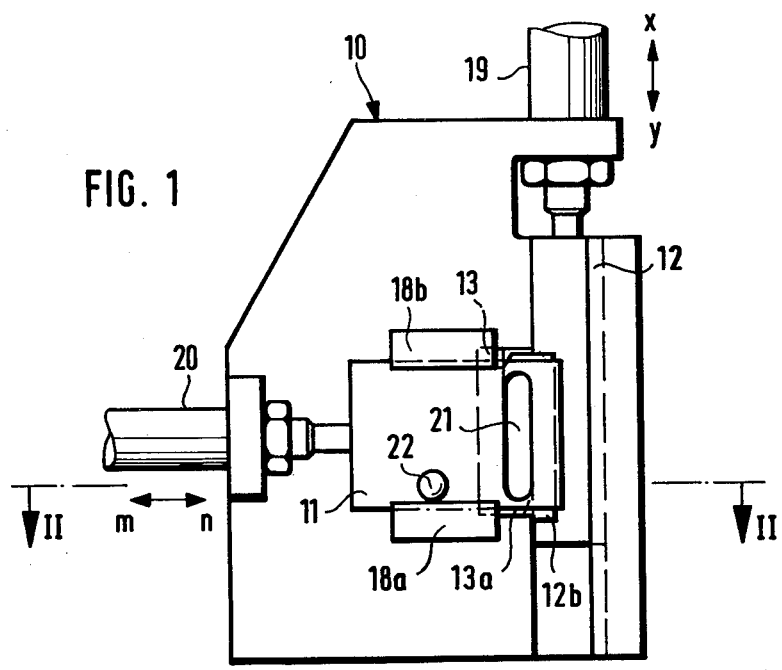
FIG. 1 is a view of the delivery device and pressing device.

FIG. 1 shows a pressing device 10 before which there is arranged in accordance with the main patent, a pre-shaping device, which, for reasons of simplification, is not represented in the drawing. Interposed between this pre-shaping device and the pressing device 10 is a delivery device 11.

The pressing device consists of a movable pressing jaw 12 and a stationary counter-holding jaw 13. Both jaws comprise a substantially L-shaped working surface, the short leg 12a, 13a of which lying against the long leg 12b, 13b of the opposite working surface. The short legs 12a, 13a comprise associated working surfaces with opposite recesses 12c, 13c, which in the open position shown in FIG. 5 form a cavity 14 of flat cross-section and with rounded-off edges for a correspondingly shaped blank 15 and, according to FIG. 8 a cylindrical cavity 16 for a completely pressed tampon 17.

The delivery device 11 is guided on its longitudinal sides in guide members 18a, 18b in the direction of the arrows m, n transversely to the direction of movement of the pressing jaw 12, wherein the drive for the reciprocating movement can be provided in a manner known per se hydraulically and/or mechanically. Components of these motion drives for the pressing jaw 12 and the delivery device 11 are shown in FIG. 1 at 19 and 20.

Figure 2:
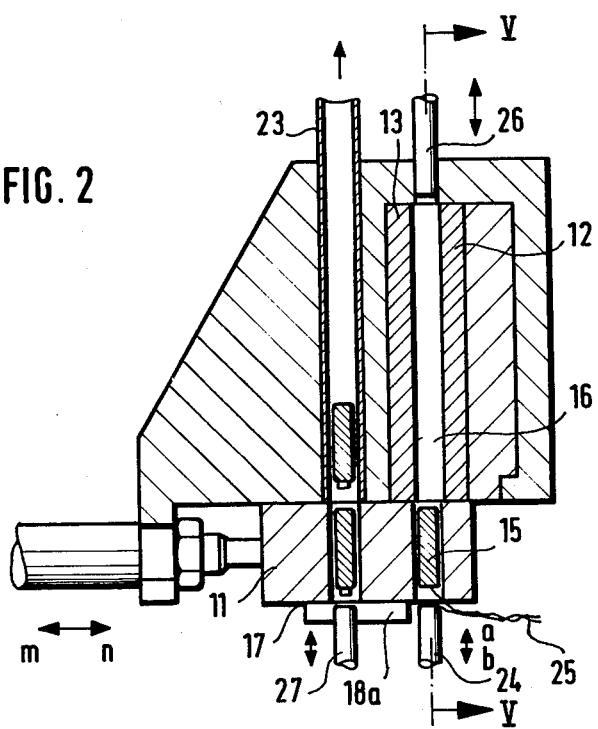
FIG. 2 is a cross-section along line II—II in FIG. 1.

The delivery device is provided with a transmitting channel 21 corresponding in cross-section to the cavity 14 of the pressing jaw 12 and the counterholding jaw 13, as well as with a receiving channel 22 of circular cross-section and a diameter corresponding approximately to that of the cavity 16 of the closed pressing jaws 12 and 13. The ejecting channel 23 is arranged in spaced relation and parallel to the transmitting channel 21, as shown in FIG. 2, the diameter of the ejecting channel corresponding to the small axis of the cross-section of the cavity 14. The tangential plane applied to the outside of the receiving channel 22 and of the transmitting channel 21 extends parallel to the direction of movement of the arrows m, n of the delivery device.

FIGS. 1, 2, and 5 show the delivery device 11 in a delivery position, in which the transmitting channel 21 is in alignment with the cavity 14 of the open pressing jaws of the pressing device 10, while the receiving channel 22 is in alignment with the ejecting channel 23 incorporated in the housing of the pressing device 10. In the longitudinal direction of the transmitting channel 21 and the cavity 14 of the open pressing jaws 12, 13 there is represented in front of the not shown pre-shaping device according to the main patent and the delivery device a transmitting device 24 formed as push-rod reciprocatingly movable in the direction of the arrows a and b. The cross-section of said transmitting device 24 corresponds approximately to that of the transmitting channel 21 but is dimensioned smaller by such an amount that a withdrawal cord 25 freely depending from the withdrawal end of the blank 15 facing the transmitting device 24 will not be sheared off or otherwise damaged when the blank is transmitted from the pre-shaping device into the transmitting channel 21 of the delivery device and into the cavity of the open pressing jaws 12, 13.

Figure 8:
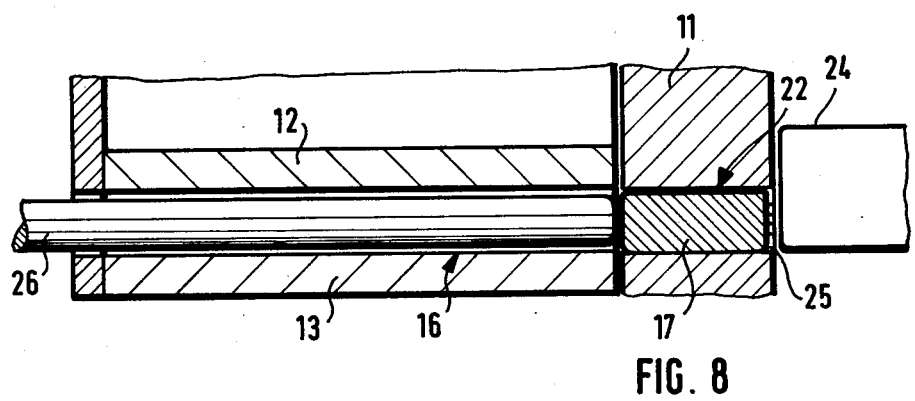
FIG. 8 shows the section according to FIG. 7 however with the tampon ejected into the receiving channel, the withdrawal cord of the tampon being pressed by the push-rod of the delivery device against the withdrawal end of the tampon.

On the side of the pressing device opposite the transmitting device 11 an ejecting device 26 formed as push-rod is provided, which is cylindrical and has a cross-section somewhat smaller than the inside cross-section of the cavity 16 of the closed pressing jaws 12, 13 of the pressing device 10. The ejecting device can, as FIG. 8 shows, be moved up to the opposite opening of the cavity of the pressing device to push the tampon 17 out of the cavity 16 of the pressing device back into the receiving channel 22 of the delivery device and thus effect a pressing of the withdrawal cord 25 against the withdrawal end, as likewise shown in FIG. 8.

FIG. 2 furthermore shows an ejecting device 27 which is arranged coaxially to the ejecting channel 23 and the receiving channel 22 and which preferably likewise consists of a push-rod. Said ejecting device 27 serves for ejecting the completely pressed tampon 17, provided with the withdrawal cord pressed thereto, through the ejecting channel 23 so that the tampon can be fed to a further processing station (not shown), for example a packing station.

Figure 6:
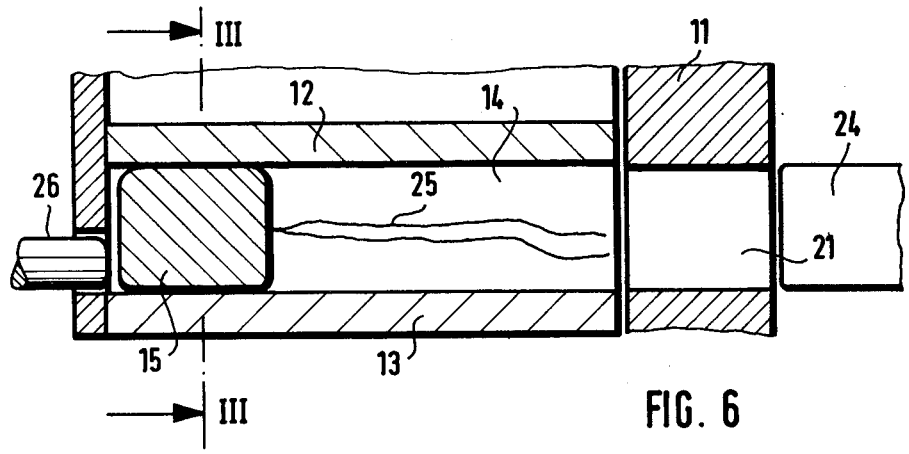
FIG. 6 shows a section according to FIG. 5, in which the push-rod of the delivery device has completely introduced the blank together with its withdrawal cord into the pressing device and has been moved back to its initial position.
Figure 7:
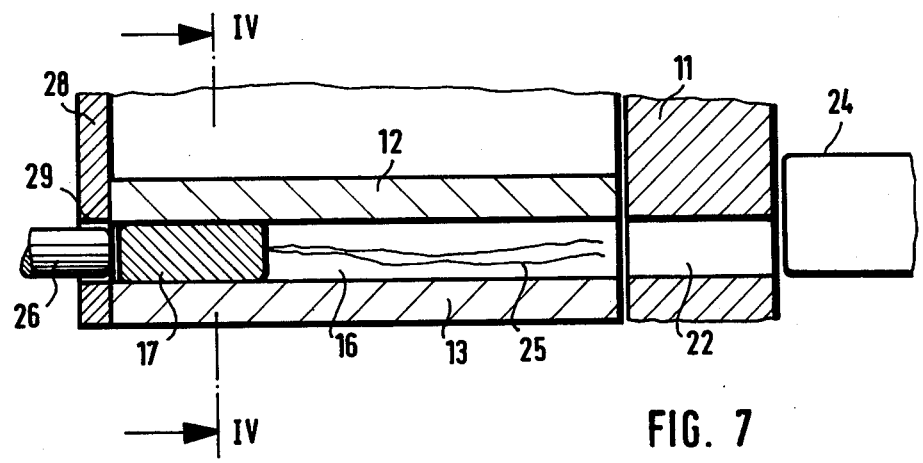
FIG. 7 shows a section according to FIGS. 5 and 6, however in the receiving position of the delivery device and with closed pressing device with completely pressed tampon.

In operation the delivery device 11 is in the position shown in FIGS. 1 and 2, in which the cotton roll, pressed flat in the pre-shaping device according to the main patent, is inserted as blank 15 through the transmitting channel 21 into the cavity 14 of the pressing device 10, the pressing jaws 12, 13 being of such width that, as apparent from FIG. 6, the withdrawal cord 25 of the blank 15 in its stretched position will lie completely within the cavity 14. The back side of the press is closed by a backplate 28 and merely comprises a bore 29 for the push-rod of the ejecting device 26. After introduction of the blank into the pressing device 10, the movable pressing jaw 12 is moved in the direction of the arrow y so that the pressing jaws take the position shown in FIG. 4 and the blank is pressed to yield the tampon 17. During the pressing process the withdrawal cord 25, as FIG. 7 shows, is completely taken along without disturbing the pressing process or being damaged thereby, which is due to the short leg 12a sliding along the working surface of the long leg 13b of the counterholding pressing jaw. Upon completion of the tampon, it is transmitted, according to FIG. 8, by means of the push-rod of the ejecting device 26 into the receiving channel 22 of the delivery device 11, which in the meantime has been moved into the receiving position in the direction of the arrow n in FIGS. 1 and 2, in which, as described, the receiving channel 22 is in alignment with the cylindrical cavity 16 of the pressing jaws 12, 13. The feed end of the receiving channel 22 is closed by the transmitting device 24 and serves as abutment for the tampon when the latter is transmitted by the push-rod of the ejecting device 26 into the receiving channel 22 of the delivery device 11 and the withdrawal cord 25 is simultaneously pressed against the withdrawal end of the tampon 17. For this purpose the push-rod of the ejecting device 26 can be axially moved for a short time beyond the normal length of the pressed tampon to ensure a sufficient pressing force for the attachment of the withdrawal cord at the front end of the tampon. For achieving a sufficient form-stability of the withdrawal cord in its pressed-on condition the push-rod of the transmitting device 24 can, if necessary, be heated.

Thereafter the delivery device is moved back to the delivery position shown in FIGS. 1 and 2, i.e., in the direction of the arrow m, so that now the receiving channel filled with the tampon 17 is disposed in the direction of flush of the ejecting channel 23 and the push-rod of the ejecting device 27 can supply the completed tampon with the pressed-on withdrawal cord through the ejecting channel 23 to a further working station. During this, the push-rod of the transmitting device 24 is completely withdrawn so that it can subsequently transfer a further blank from the pre-shaping device, according to the main patent which is flush with the working surfaces of the pressing jaws, through the delivery channel 21 into the opened pressing device 10.

In deviation from the described working method, the arrangement may be also such that in the receiving position of the delivery device in which the receiving channel 22 for receiving the pressed tampon is disposed before the cylindrical cavity 16 of the press the delivery channel 21 is filled already with a blank, which after presetting of the delivery device to the position according to FIGS. 1 and 2 is subsequently introduced into the press.

It can thus be seen that the invention permits to extend the advantages of the apparatus according to the main patent to the processability of tampon blanks already provided with a withdrawal cord, the extremely high processing quality and capacity being maintained.

I claim:

1. In an apparatus for compressing a preformed workpiece into a cylindrical tampon of the kind having an insertion end and a withdrawal end and having a withdrawal cord affixed to said withdrawal end wherein said workpiece and the withdrawal tape is introduced into a pressing device and compressed radially, the improvement comprising:

said pressing device comprising a pressing chamber having longitudinally extending walls movable with respect to each other for radially compressing said workpiece and having a first open longitudinal end and a second longitudinal end, said walls of said chamber extending longitudinally for a length sufficient to accommodate the workpiece and its extended withdrawal cord;

a delivery device adapted for reciprocating movement transversely to the longitudinally extending chamber, said delivery device having a transmitting channel and a receiving channel and positioned with respect to the pressing chamber to be reciprocated to alternately axially align each of said channels with said chamber to alternately transmit a workpiece to and alternately receive a compressed workpiece from the first open end of said pressing chamber;

means for reciprocating said delivery device to axially align said transmitting channel with said chamber;

means for urging a workpiece from said transmitting channel into said chamber and toward said second longitudinal end;

means for moving the walls of said chamber to radially compress said workpiece;

means for reciprocating said delivery device to axially align said receiving channel with said chamber; and means for ejecting said compressed workpiece into said receiving channel and pressing the withdrawal end of said ejected workpiece against a transmitting device to press the withdrawal cord against the withdrawal end of the compressed workpiece.

2. The apparatus of claim 1 wherein the walls of the pressing device comprise plates having an L-shaped transverse cross-section with the short leg of each L-shaped plate abutting the long leg of the other L-shaped plate to define the periphery of the chamber.

3. The apparatus of claim 1 wherein the means for urging the workpiece from said transmitting channel into the pressing chamber comprises a push-rod coaxially movable through the transmitting channel and into the chamber.

4. The apparatus of claim 1 wherein the pressing device is provided with a longitudinally extending ejector channel parallel to said pressing chamber and spaced therefrom so that when the transmitting channel of the delivery device is axially aligned with the pressing chamber, the receiving channel is axially aligned with the ejector channel and means are provided for urging a compressed workpiece from said receiving channel into said ejector channel.

5. The apparatus of claim 4 wherein said means for urging a compressed workpiece from said receiving channel into said ejector channel comprises a second push-rod.

6. The apparatus of claim 5 wherein the end of said second push-rod facing the receiving channel serves as the transmitting device against which the compressed workpiece is pressed when ejected from the pressing channel.

* * * * *